United States Patent
Konnai et al.

(10) Patent No.: US 11,932,544 B2
(45) Date of Patent: *Mar. 19, 2024

(54) SURFACE-MODIFIED HALLOYSITE, METHOD FOR PRODUCING SURFACE-MODIFIED HALLOYSITE, AND CATALYTIC REACTION

(71) Applicant: JFE MINERAL COMPANY, LTD., Tokyo (JP)

(72) Inventors: Hidefumi Konnai, Tokyo (JP); Shogo Shimazu, Chiba (JP)

(73) Assignee: JFE MINERAL COMPANY, LTD., Tokyo (JP)

( * ) Notice: Subject to any disclaimer, the term of this patent is extended or adjusted under 35 U.S.C. 154(b) by 911 days.

This patent is subject to a terminal disclaimer.

(21) Appl. No.: 16/344,955

(22) PCT Filed: Oct. 25, 2017

(86) PCT No.: PCT/JP2017/038513
§ 371 (c)(1),
(2) Date: Apr. 25, 2019

(87) PCT Pub. No.: WO2018/079605
PCT Pub. Date: May 3, 2018

(65) Prior Publication Data
US 2019/0270646 A1    Sep. 5, 2019

(30) Foreign Application Priority Data
Oct. 25, 2016  (JP) .................................. 2016-209031
Oct. 25, 2016  (JP) .................................. 2016-209032

(51) Int. Cl.
*C01B 33/40*  (2006.01)
*B01J 21/16*  (2006.01)
(Continued)

(52) U.S. Cl.
CPC .............. *C01B 33/26* (2013.01); *B01J 21/16* (2013.01); *B01J 35/026* (2013.01); *C01B 33/40* (2013.01);
(Continued)

(58) Field of Classification Search
CPC .................................. B01J 21/16; C01B 33/40
See application file for complete search history.

(56) References Cited

U.S. PATENT DOCUMENTS

2015/0087852 A1* 3/2015 Nair ........................ B82Y 10/00
556/173
2017/0275396 A1    9/2017 Ebisawa et al.

FOREIGN PATENT DOCUMENTS

CN     103657684 A       3/2014
CN     104119704 A  *  10/2014
(Continued)

OTHER PUBLICATIONS

Wang et al. (Sulfonated halloysite nanotubes/polyethersulfone nanocomposite membrane for efficient dye purification), Separation and Purification Technology 150 (2015) 243-251. (Year: 2015).*

(Continued)

*Primary Examiner* — Alexandre F Ferre
(74) *Attorney, Agent, or Firm* — NIXON & VANDERHYE

(57) ABSTRACT

Disclosed is a novel solid catalyst having high catalytic activity, a method for producing the solid catalyst, and a catalytic reaction using the solid catalyst. A disclosed surface-modified halloysite is a halloysite having a carboxy group-containing group or a sulfo group-containing group on the surface thereof.

18 Claims, 2 Drawing Sheets

(51) Int. Cl.
| | |
|---|---|
| B01J 35/02 | (2006.01) |
| C01B 33/26 | (2006.01) |
| C07B 61/00 | (2006.01) |
| C07D 307/46 | (2006.01) |
| C07H 3/02 | (2006.01) |

(52) U.S. Cl.
CPC ............ *C07B 61/00* (2013.01); *C07D 307/46* (2013.01); *C07H 3/02* (2013.01); *C01P 2002/82* (2013.01); *C01P 2002/88* (2013.01); *C01P 2004/13* (2013.01)

(56) References Cited

FOREIGN PATENT DOCUMENTS

| WO | WO 2009/004949 | 1/2009 |
|---|---|---|
| WO | 2016/039416 A1 | 3/2016 |

OTHER PUBLICATIONS

Matusik et al. (Surface area and porosity of nanotubes obtained from kaolin minerals of different structural order, Clays and Clay Minerals, vol. 59, No. 2, 116-135, 2011) (Year: 2011).*
Machine translation CN-104119704-A (Year: 2023).*
Office Action issued in Chinese Patent Application No. 201780065612.0 dated Nov. 26, 2021.
Wan et al., "Experimental Study on Sulphonated of HNTs," Henan Chemical Industry, No. 2, 2015, pp. 19-21.
Office Action issued in European Patent Application No. 17 865 368.9 dated Jan. 29, 2021.
Extended European Search Report, dated Oct. 8, 2019, from corresponding European patent application No. 17865368.9.
Zhang et al.; Acid-chromic chloride functionalized natural clay-particles for enhanced conversion of one-pot cellulose to 5-hydroxymethylfurfural in ionic liquids; RSC Advances; 2014; Issue 23; pp. 11664-11672.
Office Action issued in Japanese Patent Application No. 2018-547722 dated Aug. 10, 2021.
Wang et al., "Sulfonated halloysite nanotubes/polyethersulfone nanocomposite membrane for efficient dye purification," Journal of Membrane Science, Jun. 6, 2015, vol. 150, pp. 243-251.
Shinozuka et al., "Synthesis and behavior as solid acid catalyst of Sulfonated Allophane," Clay Science Debate Lecture Summaries, vol. 52, 2008, pp. 114-115.
Ishizaki et al., "Synthesis of 5-hydroxymethylfurfural from fructose in 2-propanol by sulfonated clay catalyst," Proceedings of Symposium of the Chemical Society of Japan (Chemical Society of Japan Annual Convention Lecture Proceedings) (Spring and Autumn), 2012, No. 92, pp. 458.
International Search Report, PCT/JP2017/038513, dated Dec. 12, 2017.
Joo, Yongho, et al., "Aggregation and Stabilization of Carboxylic Acid Functionalized Halloysite Nanotubes (HNT-COOH)", The Journal of Physical Chemistry C, Jul. 16, 2012, 116, pp. 18230-18235.
Liu, Xin, et al., "Proton conductivity improvement of sulfonated poly (ether ether ketone) nanocomposite membranes with sulfonated halloysite nanotubes prepared via dopamine-initiated atom transfer radical polymerization", Journal of Membrane Science, Jan. 13, 2016, 504, pp. 206-219.
K. Yabushita et al., "A Study on Catalytic Conversion of Non-Food Biomass into Chemicals", Springer Singapore, 2016, p. 43-75.
X. Qi et al., "Bioresource Technology", Hydrolysis of cellulose over functionalized glucose-derived carbon catalyst in ionic liquid:, 2012, vol. 116, p. 355-359.
Ken-ichi Shimizu et al., "Catalysis Communications", "Enhanced production of hydroxymethylfurfural from frucose with solid acid catalysts by simple water removal methods", Aug. 25, 2009, vol. 10, No. 14, p. 1849-1853.

* cited by examiner

SURFACE-MODIFIED HALLOYSITE, METHOD FOR PRODUCING SURFACE-MODIFIED HALLOYSITE, AND CATALYTIC REACTION

TECHNICAL FIELD

The present invention relates to a surface-modified halloysite, a method for producing surface-modified halloysite, and a catalytic reaction.

BACKGROUND ART

As methods to synthesize glucose by hydrolyzing cellulose, a method that uses carbon activated by alkali as a solid catalyst (Non-Patent Literature 1) and a method that uses sulfonated carbon (Non-Patent Literature 2) have been proposed.

Furthermore, as a method of synthesizing hydroxymethylfurfural (HMF), which is expected to be utilized as a biofuel and a plastic precursor, from fructose, which is a naturally occurring saccharide, a method that uses an acid catalyst in a dimethyl sulfoxide (DMSO) solvent has been proposed (Non-Patent Literature 3).

CITATION LIST

Non-Patent Literature

Non-Patent Literature 1: K. Yabushita et al., "A Study on Catalytic Conversion of Non-Food Biomass into Chemicals", Springer Singapore, 2016, p. 43-75
Non-Patent Literature 2: X. Qi et al., "Bioresource Technology", 2012, Vol. 116, p. 355-359
Non-Patent Literature 3: Ken-ichi Shimizu and two others, "Catalysis Communications", Aug. 25, 2009, Vol. 10, No. 14, p. 1849-1853

SUMMARY OF INVENTION

Technical Problems

However, there is a disadvantage of difficult separation and recovery of the solvent when a reaction is performed in a DMSO solvent by using an acid catalyst. Therefore, in reactions such as the synthesis reaction described above, development of a solid catalyst that achieves high activity in a general-purpose solvent and that is easily separated and recovered has been demanded.

An object of the present invention is to provide a novel solid catalyst having high catalytic activity similarly to those of Non-Patent Literatures 1 to 3, a method for producing the solid catalyst, and a catalytic reaction using the solid catalyst.

Solution to Problems

As a result of diligent research to solve the problems described above, the inventors of the present invention found that halloysite having a carboxy group-containing group or a sulfo group-containing group on its surface exhibits high catalytic activity, and thus completed the present invention.

Specifically, the present inventors discovered that the above problems can be solved by the following configuration.

(1) A surface-modified halloysite having a carboxy group-containing group or a sulfo group-containing group on its surface.
(2) The surface-modified halloysite described in (1) above further having a hydroxy group on its surface.
(3) The surface-modified halloysite described in (1) or (2) above,
 wherein at least part of the surface-modified halloysite is in nanotube form.
(4) A surface-modified halloysite producing method comprising reacting halloysite with a carboxylic anhydride or a cyclic sulfonic acid ester to thereby produce the surface-modified halloysite described in (1) or (2) above.
(5) A surface-modified halloysite producing method comprising reacting halloysite containing halloysite in nanotube form with a carboxylic anhydride or a cyclic sulfonic acid ester to thereby produce the surface-modified halloysite described in (3) above.
(6) A catalytic reaction using the surface-modified halloysite described in any one of (1) to (3) as a solid catalyst.
(7) The catalytic reaction described in (6) above,
 wherein, using the surface-modified halloysite described in any one of (1) to (3) above as a solid catalyst, a polysaccharide is hydrolyzed to synthesize a monosaccharide or fructose is dehydrated and decomposed to synthesize hydroxymethylfurfural.

Advantageous Effects of Invention

As described below, according to the present invention, a novel solid catalyst having high catalytic activity (e.g., high yield, high selectivity, and high reaction conversion rate; especially high yield), a method for producing the solid catalyst, and a catalytic reaction using the solid catalyst can be provided.

DESCRIPTION OF EMBODIMENTS

Figure 1:
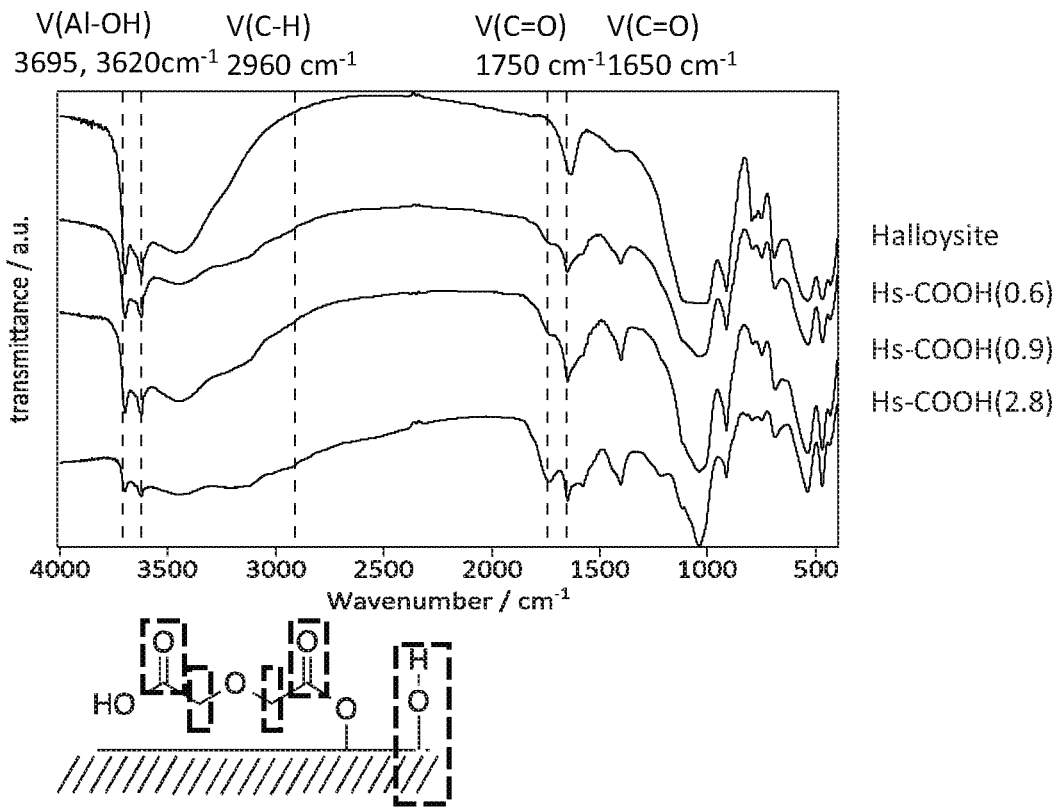
FIG. 1 shows FT-IR spectra of halloysite before and after surface modification.

The surface-modified halloysite of the present invention, a method for producing the surface-modified halloysite, and a catalytic reaction that uses the surface-modified halloysite are described below.

Note that the numerical range represented by using "(from) . . . to . . . " in the present specification means a range that includes the numerical values shown before and after "to" as the lower limit value and the upper limit value.

[Surface-Modified Halloysite]

The surface-modified halloysite of the present invention (hereinafter, also referred to as "halloysite of the present invention" or "surface-modified halloysite") is halloysite having a carboxy group (—COOH)-containing group or a sulfo group (—SO$_3$H)-containing group on its surface. Note that, hereinafter, the halloysite having a carboxy group-containing group on its surface is also referred to as "Hs—COOH", and halloysite having a sulfo group-containing group on its surface is also referred to as "Hs-PS".

The halloysite of the present invention has a structure in which a carboxy group-containing group or a sulfo group-containing group is bonded to the surface of the halloysite having a fine structure (e.g., nanotube form or the like), and thus the fine structure serves as a reactive site. It is presumed that, as a result, extremely high catalytic activity is achieved.

Note that the halloysite is a clay mineral represented by $Al_2Si_2O_5(OH)_4 \cdot 2H_2O$ or $Al_2Si_2O_5(OH)_4$. The halloysite may contain halloysite in nanotube form (halloysite nanotube). The halloysite nanotube generally has a hollow tube-like structure in submicron size, and the outer surface thereof is mainly formed from silicate $SiO_2$ and the inner surface thereof is mainly formed from alumina $Al_2O_3$.

From the perspective of achieving even superior effect of the present invention, at least a part of the halloysite of the present invention is preferably in the nanotube form described above. Examples of other forms include sheet form, spherical form, lump form having sharp corners, plate form, and the like.

When the halloysite of the present invention has a nanotube form, the length of the nanotube is preferably from 2 to 1000 nm, and more preferably from 2 to 500 nm, from the perspective of achieving even superior effect of the present invention.

Furthermore, when the halloysite of the present invention has a nanotube form, the inner diameter of the nanotube is preferably from 2 to 200 nm, and more preferably from 2 to 100 nm, from the perspective of achieving even superior effect of the present invention.

Furthermore, at least part of the halloysite of the present invention is preferably formed from surface-modified halloysite in nanotube form, and the agglomerate thereof may be in the form of powder or a granulated substance. In the case of the granulated substance, granulation process may be appropriately added before the surface modification or before use as a solid catalyst or the like. Examples of the form of the granulated substance at this time include cylindrical pellets, spherical forms, granules, flake forms, and the like. As a method of granulation, a publicly known method such as extrusion, tumbling, and spray drying can be applied.

The position where a carboxy group-containing group or a sulfo group-containing group is placed in the halloysite of the present invention is not particularly limited as long as the position is on the surface of the halloysite. However, when the halloysite of the present invention is in nanotube form, the position is preferably on the inner surface of the nanotube from the perspective of achieving even superior effect of the present invention.

Furthermore, the bonding form of a carboxy group-containing group or a sulfo group-containing group to the surface is not particularly limited but is preferably covalent bonding from the perspective of achieving even superior effect of the present invention. When the bonding form is covalent bonding, carboxy group-containing groups or sulfo group-containing groups are less likely to flow out (for instance, a surface modification agent described below is less likely to flow out) into the solvent during catalytic reaction, and as a result, the halloysite of the present invention exhibits higher catalytic activity. This is particularly apparent in the case where the solvent used in the catalytic reaction is a polar solvent (e.g., water, methanol, ethanol).

In the case where the halloysite of the present invention has a carboxy group-containing group, the carboxy group-containing group contained in the halloysite of the present invention is a carboxy group or a group containing a carboxy group. The carboxy group-containing group is preferably a group represented by -L-COOH from the perspective of achieving even superior effect of the present invention. Note that L represents a single bond or a divalent organic group.

Examples of the divalent organic group include substituted or unsubstituted divalent aliphatic hydrocarbon groups (e.g., alkylene groups; preferably having from 1 to 8 carbon atoms), substituted or unsubstituted divalent aromatic hydrocarbon groups (e.g., arylene groups; preferably having from 6 to 12 carbon atoms), —O—, —S—, —SO$_2$—, —NR— (R: hydrocarbon group), —SiR$^1$R$^2$— (R$^1$ and R$^2$: hydrocarbon group), —CO—, —NH—, —COO—, —CONH—, groups formed from combinations of these (e.g., alkyleneoxy groups, alkyleneoxy carbonyl groups, alkylene carbonyloxy groups), and the like.

In the case where the halloysite of the present invention has a sulfo group-containing group, the sulfo group-containing group contained in the halloysite of the present invention is a sulfo group or a group containing a sulfo group. The sulfo group-containing group is preferably a group represented by -L-SO$_3$H from the perspective of achieving even superior effect of the present invention. Note that L represents a single bond or a divalent organic group.

The specific examples and preferable embodiments of the divalent organic groups are the same as those for the carboxy group-containing group described above. The divalent organic group is preferably a divalent aliphatic hydrocarbon group from the perspective of achieving even superior effect of the present invention.

In the case where the halloysite of the present invention contains a carboxy group-containing group, in the halloysite of the present invention, the carboxy group-containing group content (hereinafter, also referred to as "carboxy group content") relative to the entire surface-modified halloysite is not particularly limited; however, the content is preferably from 0.1 to 15 mmol/g, more preferably from 0.1 to 12 mmol/g, and even more preferably from 0.1 to 10 mmol/g, from the perspective of achieving even superior effect of the present invention. Among these, the content is preferably 0.7 mmol/g or greater, and more preferably 1.0 mmol/g or greater, from the perspective of achieving even superior effect of the present invention.

In the case where the halloysite of the present invention contains a sulfo group-containing group, in the halloysite of the present invention, the sulfo group-containing group content (hereinafter, also referred to as "sulfo group content") relative to the entire surface-modified halloysite is not particularly limited; however, the content is preferably from 0.1 to 15 mmol/g, more preferably from 0.1 to 12 mmol/g, and even more preferably from 0.1 to 10 mmol/g, from the perspective of achieving even superior effect of the present invention.

The halloysite of the present invention preferably further has a hydroxy group on its surface from the perspective of achieving even superior effect of the present invention. In particular, from the perspective of achieving even superior effect of the present invention, the carboxy group-containing groups or the sulfo group-containing groups described above, and the hydroxy groups preferably coexist uniformly on the surface.

[Method for Producing Surface-Modified Halloysite]

The method for producing the halloysite of the present invention is not particularly limited; however, from the perspective of achieving even superior activity of the resulting surface-modified halloysite, one exemplary method is a method in which a halloysite (surface-unmodified halloysite) (hereinafter, the surface-unmodified halloysite is also simply referred to as "halloysite" or "Hs") and a surface modification agent described below are reacted. In particular, from the perspective of achieving even superior activity of the resulting surface-modified halloysite, a method in which part of the hydroxy groups on the surface of the halloysite is reacted with the surface modification agent is preferable. It is conceived that a surface-modified halloysite in which the carboxy group-containing groups or the sulfo group-containing groups and the hydroxy groups uniformly coexist can be obtained by performing the reaction as described above.

More specifically, a method in which the halloysite and the surface modification agent are agitated in the solvent under a high temperature (e.g., from 50 to 200° C.) condition can be employed, for instance.

Although the solvent is not particularly limited, the solvent is preferably an organic solvent, and more preferably toluene, from the perspective of achieving even superior activity of the resulting surface-modified halloysite.

The halloysite is surface-modified by the method described above. More specifically, the carboxy group-containing groups or the sulfo group-containing groups are introduced into the surface of the halloysite (e.g., in the case where the halloysite is in nanotube form, into alumina of the inner surfaces of the nanotubes).

[Halloysite]

The halloysite (surface-unmodified halloysite) is not particularly limited but preferably contains halloysite in nanotube form (halloysite nanotube) from the perspective of achieving even superior activity of the resulting surface-modified halloysite. Examples of other forms of the halloysite include sheet form, spherical form, lump form having sharp corners, plate form, and the like. The specific examples and preferable embodiments of the form of the halloysite (length, inner diameter, and the like of the halloysite nanotube) are the same as those for the halloysite of the present invention described above.

Halloysite generally has a hydroxy group (OH group) on its surface.

The amount of the hydroxy groups present on the surface of the halloysite (surface-unmodified halloysite) (surface hydroxy group amount) is not particularly limited but is preferably from 0.1 to 15 mmol/g from the perspective of achieving even superior activity of the resulting surface-modified halloysite. Note that the surface hydroxy group amount of the halloysite is measured by methyl lithium (MeLi) titration (Shimazu et al., Journal of Molecular Catalysis A: Chemical, 182-183, 343-350 (2002)).

The quartz content of the halloysite is preferably 1.00 mass % or less, more preferably 0.70 mass % or less, and even more preferably 0.40 mass % or less, from the perspective of achieving even superior activity of the resulting surface-modified halloysite. The lower limit is not particularly limited, but it is preferable that no quartz be detected in XRD measurement.

The quartz content of halloysite powder is determined by XRD measurement as described below.

First, a filter for sample collection (fluororesin-treated glass fiber filter) is weighed. Thereafter, the filter is placed in a Zn cell for XRD measurement, and the range including the angle at which Zn is detected (2θ=43.2 deg) is measured by XRD.

Thereafter, the sample (halloysite powder and quartz reference standards which are samples for creating a calibration curve) is dispersed in water. Specifically, approximately 15 mg of the halloysite powder is dispersed in pure water. Similarly, approximately 0.1 mg, 0.5 mg, 1.0 mg, 3.0 mg, and 5.0 mg of quartz reference standards (Japan Association for Working Environment Measurement, JAWE 460 for free silicic acid analysis) are dispersed in pure water.

By suction filtration, the sample dispersed in the water is collected on the filter, which has been measured by XRD in advance. The collected sample is, together with the filter, dried at 105° C. for 2 hours, and then weighed. The mass of the collected sample is calculated by subtracting the mass of the filter weighed in advance.

The weighed sample is, together with the filter, placed in a Zn cell, and the range including the angle at which the quartz is detected (first intense line 2θ=26.6 deg) and the angle at which Zn derived from the cell is detected (2θ=43.2 deg) is measured by XRD.

By the base standard absorption correction method, the peak integrated intensity of the quartz is corrected by using the peak integrated intensity of a Zn plate (base standard plate).

A calibration curve of the mass is created from the peak integrated intensities of the quartz reference standards, and the quantitative value of the quartz in the halloysite powder is calculated by using the calibration curve. Thus, the quartz content of the halloysite powder is determined.

Other specific conditions in the XRD analysis are as described below.

Used instrument: X-ray diffractometer SmartLab (available from Rigaku Corporation)
X-ray tube: CuKα
Optical system: Bragg-Brentano geometry
Tube voltage: 45 kV
Tube current: 200 mA
Detector: One-dimensional semiconductor detector
Scanning range: 26.0 to 28.0 deg
Scanning step: 0.01 deg
Scanning speed: 5 deg/min <Purified Halloysite>

The halloysite is preferably purified halloysite from the perspective of achieving even superior activity of the resulting surface-modified halloysite. The degree of purification is appropriately selected in view of the purpose of use, performance, production cost, and the like.

The method for purifying halloysite is not particularly limited; however, in order to remove coexisting minerals other than halloysite and obtain a greater amount of halloysite nanotube particles, a method that uses wet elutriation or centrifugal separation is preferable.

Examples of the method of drying a slurry of purified halloysite obtained by the method described above include:

(1) drying by spreading the slurry over a porous sheet or filter cloth;

(2) obtaining an aggregated slurry through pH adjustment, addition of an aggregating agent, or the like, subsequently obtaining a cake by dehydrating the slurry through filtration under reduced pressure, filtration under pressure, centrifugal separation, or the like, and then drying the cake; or (3) directly drying by freeze-drying, media slurry drying, drying with a spray dryer, or the like.

Note that, after the drying, in order to break down the agglomerates or granules formed by the drying, pulverization may be performed to form powder.

PREFERRED EMBODIMENT

From the perspective of achieving even superior activity of the resulting surface-modified halloysite, the halloysite is preferably halloysite powder (hereinafter, also referred to as "halloysite powder of the present invention" or "powder of the present invention") containing granules formed by causing halloysite containing halloysite nanotubes to aggregate, the granules having first pores derived from tube pores of the halloysite nanotubes and second pores that are different from the first pores.

Furthermore, the halloysite powder of the present invention has the following advantages:

Having high handleability due to high bulk specific gravity and low dusting characteristics Suitable for mass production due to excellent flowability and excellent supply capacity.

That is, the halloysite powder of the present invention has high handleability and excellent supply capacity, and what is more, the presence of the second pores allows a solution to penetrate to the nanotubes constituting the granules, which makes surface modification possible.

It is possible to confirm from, for example, a scanning electron microscope (SEM) photograph that the granules contained in the powder of the present invention (hereinafter, also referred to as "granules of the present invention") are granules formed by causing halloysite containing halloysite nanotubes to aggregate and have pores derived from tube pores of the halloysite nanotubes (first pores).

It is also possible to confirm from, for example, an SEM photograph of a cross section of the granule of the present invention that the granule of the present invention has second pores that are different from the first pores. The cross section of the granule is exposed by processing the granule with focused ion beam (FIB). Furthermore, the fact above can also be confirmed by means of pore distribution measurement.

(Method for Producing Halloysite Powder of Embodiment of the Present Invention)

The method for producing the halloysite powder of the present invention is not particularly limited but, preferably, is a method for producing the halloysite powder of the present invention described above and at least comprises a step of preparing a slurry of halloysite containing halloysite nanotubes (slurry preparation step) and a step of preparing powder from the slurry (powder preparation step).

Examples of the powder preparation step include a step in which powder is obtained by subjecting the slurry prepared in the slurry preparation step (e.g., a dispersion phase obtained through centrifugal separation) to media slurry drying, drying with a spray dryer, or the like.

Note that the means for preparing powder from the slurry is not limited to the media slurry drying and drying with a spray dryer described above.

The production method of the present invention may further comprise a step of firing the powder obtained in the powder preparation step (firing step).

[Surface Modification Agent]

The surface modification agent is not particularly limited as long as the surface modification agent is a compound that can introduce carboxy group-containing groups or sulfo group-containing groups onto the surface of halloysite.

The compound that can introduce carboxy group-containing groups onto the surface of halloysite (hereinafter, also referred to as "carboxy group-containing group-introducing surface modification agent") is not particularly limited but is preferably at least one type of compound selected from the group consisting of carboxylic acid, carboxylate, and carboxylic anhydride, from the perspectives of causing energy saving and efficient reaction (reacting with OH groups on the surface of the halloysite in one process, and generating carboxy group-containing groups bonded to Al—O at their one ends) and achieving even superior activity of the resulting surface-modified halloysite. The carboxy group-containing group-introducing surface modification agent is preferably a carboxylic anhydride from the perspective of achieving even superior activity of the resulting surface-modified halloysite.

Examples of the carboxylic anhydride include succinic anhydride, maleic anhydride, glutaric anhydride, itaconic anhydride, citraconic anhydride, tetrahydrophthalic anhydride, hexahydrophthalic anhydride, 4-methyltetrahydrophthalic anhydride, 4-methylhexahydrophthalic anhydride, 3-methyltetrahydrophthalic anhydride, dodecenylsuccinic anhydride, phthalic anhydride, diglycolic anhydride, glutaric anhydride, and the like. Among these, diglycolic anhydride is preferable from the perspectives of reacting with the OH groups on the surface of the halloysite so that one end is bonded to O and the other end generates a carboxylic acid group and achieving even superior activity of the resulting surface-modified halloysite.

The added amount of the carboxy group-containing group-introducing surface modification agent relative to the halloysite is preferably from 1 to 1000 equivalents, and more preferably from 1 to 100 equivalents, relative to the surface hydroxy group amount of the halloysite from the perspective of achieving even superior activity of the resulting surface-modified halloysite. Furthermore, the added amount of the carboxy group-containing group-introducing surface modification agent relative to the halloysite is preferably from 1 to 1000 mmol, more preferably from 1 to 200 mmol, and even more preferably from 1 to 100 mmol, per 1 g of the halloysite (surface-unmodified halloysite) from the perspective of achieving even superior activity of the resulting surface-modified halloysite.

The substitution rate of Hs—COOH is not particularly limited but is preferably from 1 to 99 mol %, more preferably from 10 to 90 mol %, even more preferably from 20 to 80 mol %, and particularly preferably from 30 to 80 mol %, from the perspective of achieving even superior activity of the resulting surface-modified halloysite.

Note that the substitution rate of Hs—COOH refers to a proportion of the carboxy group content (mmol/g) of the Hs—COOH relative to the surface hydroxy group amount (mmol/g) of the halloysite (surface-unmodified halloysite) in the Hs—COOH obtained by reacting a part of the hydroxy groups of the surface of the halloysite (surface-unmodified halloysite) with the surface modification agent.

The compound that can introduce sulfo group-containing groups onto the surface of halloysite (hereinafter, also referred to as "sulfo group-containing group-introducing surface modification agent") is not particularly limited but is preferably at least one type of compound selected from the group consisting of sulfonic acid, sulfonic acid salt, and sulfonic acid ester, from the perspective of achieving even superior activity of the resulting surface-modified halloysite. The sulfo group-containing group-introducing surface modification agent is preferably a sulfonic acid ester, and more preferably a cyclic sulfonic acid ester, from the perspectives of causing energy saving and efficient reaction (reacting with OH groups on the surface of the halloysite in one process, and generating sulfo group-containing groups bonded to Al—O at their one ends) and achieving even superior activity of the resulting surface-modified halloysite.

Examples of the cyclic sulfonic acid ester include 1,3-propanesultone, 1,2-propanesultone, 1,4-butanesultone, 1,2-butanesultone, 1,3-butanesultone, 2,4-butanesultone, 1,3-pentanesultone, and the like. Among these, 1,3-propanesultone is preferable from the perspective of achieving even superior activity of the resulting surface-modified halloysite.

The added amount of the sulfo group-containing group-introducing surface modification agent relative to the halloysite is preferably from 1 to 1000 equivalents, and more preferably from 1 to 100 equivalents, relative to the surface hydroxy group amount of the halloysite from the perspective of achieving even superior activity of the resulting surface-modified halloysite. Furthermore, the added amount of the sulfo group-containing group-introducing surface modification agent relative to the halloysite is preferably from 1 to 1000 mmol, more preferably from 1 to 200 mmol, and even more preferably from 1 to 100 mmol, per 1 g of the halloysite (surface-unmodified halloysite) from the perspective of achieving even superior activity of the resulting surface-modified halloysite.

The substitution rate of Hs-PS is not particularly limited but is preferably from 1 to 99 mol %, more preferably from 10 to 90 mol %, even more preferably from 20 to 80 mol %, and particularly preferably from 30 to 80 mol %, from the perspective of achieving even superior activity of the resulting surface-modified halloysite.

Note that the substitution rate of Hs-PS refers to a proportion of the sulfo group content (mmol/g) of the Hs-PS relative to the surface hydroxy group amount (mmol/g) in the halloysite (surface-unmodified halloysite) in the Hs-PS obtained by reacting part of the hydroxy groups of the surface of the halloysite (surface-unmodified halloysite) with the surface modification agent.

[Catalytic Reaction]

The catalytic reaction of the present invention is a catalytic reaction that uses the halloysite of the present invention described above as a solid catalyst. As described above, the halloysite of the present invention has a structure in which carboxy group-containing groups or sulfo group-containing groups are bonded to the surface of the halloysite having a fine structure (e.g., nanotube form or the like), and thus the halloysite is significantly advantageous for acid catalytic reaction (e.g., conventionally known acid catalytic reaction).

In particular, in the case where the halloysite of the present invention is halloysite having a carboxy group-containing group on its surface, the halloysite is significantly advantageous for a method for synthesizing a monosaccharide by hydrolyzing a polysaccharide (including oligosaccharides of disaccharides and the like).

Furthermore, in the case where the halloysite of the present invention is halloysite having a sulfo group-containing group on its surface, the halloysite is advantageous for dehydration and decomposition of saccharides and, in particular, is significantly advantageous for a method of synthesizing hydroxymethylfurfural by dehydrating and decomposing fructose.

In the case where the halloysite of the present invention is halloysite having a sulfo group-containing group on its surface, the solvent used in the catalytic reaction is not particularly limited but is preferably an organic solvent, more preferably an alcohol (particularly, having from 1 to 10 carbon atoms), even more preferably an alcohol having at least 3 carbon atoms, and particularly preferably an alcohol having at least 4 carbon atoms (butanol (e.g., 2-butanol)), from the perspective of enhancing yield.

The reaction time of the catalytic reaction of the present invention is not particularly limited but is preferably 1 hour or longer, more preferably 3 hours or longer, and even more preferably 10 hours or longer, from the perspective of enhancing yield. The upper limit is not particularly limited but is preferably 100 hours or less.

EXAMPLES

The present invention will be described in further detail through examples below, but the present invention is not limited thereto.

[Preparation and the Like of Purified Halloysite]

Purified halloysites (purified halloysites 1 and 2) were prepared as described below. Note that it was confirmed with SEM photographs that the purified halloysites 1 and 2 met the definition of the powder of the present invention described above.

<Purified Halloysite 1>

Clay (Iide clay) produced in Osodani factory (Osodani, Iidemachi, Nishiokitamagun Yamagata) of Iide Mining Works of JFE Mineral Company Ltd. was used as a raw material. This clay contains halloysite and very fine sand represented by $SiO_2$ (quartz) as the main components.

First, the Iide clay and water were placed in a high-speed mixer, and a slurry in which the Iide clay was dispersed in water was obtained.

Thereafter, all of the slurry was passed through a sieve having an opening of 45 μm to remove coarse particles having a size greater than 45 μm on the sieve. The slurry having a size less than 45 μm having passed through the sieve was filtrated with suction, and the residue on the filter was recovered as a dehydrated cake.

Furthermore, in a high-speed mixer, the dehydrated cake and water were added, and then an anionic polymeric surfactant was added as a dispersant to obtain a dispersed slurry.

The obtained dispersed slurry was separated into a sedimentation phase and a dispersion phase by the centrifugal force of 2470 G using a centrifuge. Then, the dispersion phase was collected by sucking up the portion that is above the precipitate phase by a pump.

Then, the obtained slurry of the dispersion phase was dried by a media slurry dryer to obtain granular halloysite powder. The granular halloysite powder was fired at 400° C. to remove the dispersant, thus removing the surfactant. A purified halloysite was prepared as described above. The obtained purified halloysite was used as the purified halloysite 1.

The obtained purified halloysite 1 contained halloysite in nanotube form (halloysite nanotubes). Furthermore, the obtained purified halloysite 1 contained hydroxy groups on its surface. The surface hydroxy group amount of the halloysite was measured, and the amount was 3.55 mmol/g. The measurement method of the surface hydroxy group amount of the halloysite was as described above.

<Purified Halloysite 2>

A purified halloysite was prepared by the same procedure as that for the purified halloysite 1 except for performing the drying by using a spray dryer in place of the media slurry dryer. The obtained purified halloysite was used as the purified halloysite 2.

The obtained purified halloysite 2 contained halloysite in nanotube form (halloysite nanotubes). The obtained purified halloysite 2 also contained hydroxy groups on its surface. The surface hydroxy group amount of the halloysite was measured, and the amount was 3.55 mmol/g. The measurement method of the surface hydroxy group amount of the halloysite was as described above.

<Halloysite Available from Sigma-Aldrich>

As a commercially available halloysite, halloysite in powder form (available from Sigma-Aldrich; product number: 685445; containing nanotube-shaped halloysite (halloysite nanotubes)) was used. The halloysite available from Sigma-Aldrich was in powder form, and it was confirmed with an SEM photograph that the halloysite did not meet the definition of the powder of the present invention described above.

Figure 2:
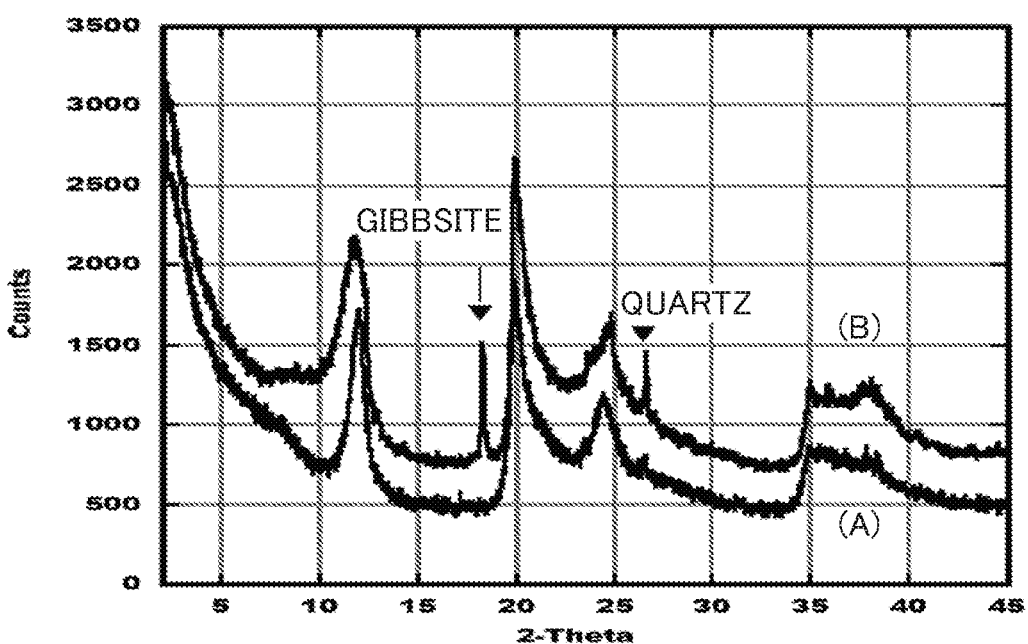
FIG. 2 shows XRD patterns of halloysites used in Examples.

FIG. 2 shows XRD patterns of the halloysites (halloysites before surface modification) used in Examples.

(A) is the XRD pattern of the purified halloysite 1 described above, and (B) is the XRD pattern of the halloysite available from Sigma-Aldrich described above. Note that the purified halloysite 2 showed an XRD pattern similar to that of the purified halloysite 1. While the peaks of gibbsite and quartz appeared in the XRD pattern of the halloysite available from Sigma-Aldrich (B), no gibbsite peak was detected and the peak of quartz was significantly low in the XRD pattern of the purified halloysites 1 and 2 (A). Therefore, it can be said that the purified halloysites 1 and 2 had a small amount of impurities such as gibbsite and quartz and were highly pure.

When the quartz contents of the purified halloysites 1 and 2 and the halloysite available from Sigma-Aldrich were measured, the quartz content of each of the purified halloysites 1 and 2 was 0.3 mass %, and the quartz content of the halloysite available from Sigma-Aldrich was 1.2 mass %.

[Production of Surface-Modified Halloysite]

Surface-modified halloysites (Hs—COOH) (Examples 1-1 to 1-4 and Examples 1-6 and 1-7) and surface-modified halloysites (Hs-PS) (Examples 2-1 and 2-2 and Examples 2-7 and 2-8) were produced as described below.

Example 1-1

The obtained purified halloysite 1 was dried at 150° C. for 1 hour. To the dried purified halloysite 1 (0.20 g), 40 mL of anhydrous toluene and 1.27 mmol of diglycolic anhydride (1,4-dioxane-2,6-dione) (its structural formula being shown below) (1.8 equivalents relative to the surface hydroxy group amount of the halloysite) were added. Furthermore, 0.25 mmol of N,N-dimethyl-4-aminopyridine (DMAP) (catalytic amount) and 2.5 mmol of triethylamine (NEt$_3$) (base) were added, and the mixture was subjected to ultrasonic treatment for 1 hour and then agitated while being refluxed (70° C., 72 hours). Subsequently, after the filtration, the resultant was washed with distilled water and subjected to drying treatment. Thus, the purified halloysite 1 was surface-modified.

[Chemical Formula 1]

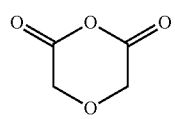

From the FT-IR measurement (FIG. 1), it was confirmed that the halloysite after the surface modification was halloysite having carboxy group-containing groups (—COCH$_2$OCH$_2$—COOH) on the inner surfaces of the halloysite nanotubes (surface-modified halloysite). Note that each carboxy group-containing group was bonded to the alumina on the inner surface of the halloysite nanotube and formed a structure represented by Al—O—COCH$_2$OCH$_2$—COOH.

When the thermogravimetry-differential thermal analysis (TG-DTA) was performed on the obtained surface-modified halloysite, the carboxy group content was estimated as 0.6 mmol/g.

Example 1-2

The purified halloysite 1 was surface-modified by the same procedure as in Example 1-1 except for changing the added amount of the diglycolic anhydride to 1.90 mmol, changing the added amount of the N,N-dimethyl-4-aminopyridine (DMAP) to 0.37 mmol, and changing the added amount of the triethylamine (NEt$_3$) (base) to 3.7 mmol.

From the FT-IR measurement (FIG. 1), it was confirmed that the halloysite after the surface modification was halloysite having carboxy group-containing groups (—COCH$_2$OCH$_2$—COOH) on the inner surfaces of the halloysite nanotubes (surface-modified halloysite). Note that each carboxy group-containing group was bonded to the alumina on the inner surface of the halloysite nanotube and formed a structure represented by Al—O—COCH$_2$OCH$_2$—COOH.

When the thermogravimetry-differential thermal analysis (TG-DTA) was performed on the obtained surface-modified halloysite, the carboxy group content was estimated as 0.9 mmol/g.

Example 1-3

The purified halloysite 1 was surface-modified by the same procedure as in Example 1-1 except for changing the added amount of the diglycolic anhydride to 2.53 mmol, changing the added amount of the N,N-dimethyl-4-aminopyridine (DMAP) to 0.5 mmol, and changing the added amount of the triethylamine (NEt$_3$) (base) to 5.0 mmol.

From the FT-IR measurement (FIG. 1), it was confirmed that the halloysite after the surface modification was halloysite having carboxy group-containing groups (—COCH$_2$OCH$_2$—COOH) on the inner surfaces of the halloysite nanotubes (surface-modified halloysite). Note that each carboxy group-containing group was bonded to the alumina on the inner surface of the halloysite nanotube and formed a structure represented by Al—O—COCH$_2$OCH$_2$—COOH.

When the thermogravimetry-differential thermal analysis (TG-DTA) was performed on the obtained surface-modified halloysite, the carboxy group content was estimated as 2.8 mmol/g.

Note that, in FIG. 1, "Halloysite" is the spectrum obtained by Fourier Transform Infrared Spectroscopy (FT-IR) before the surface modification (purified halloysite 1), "Hs—COOH (0.6)" is the FT-IR spectrum after the surface modification (Example 1-1), "Hs—COOH (0.9)" is the FT-IR spectrum after the surface modification (Example 1-2), and "Hs—COOH (2.8)" is the FT-IR spectrum after the surface modification (Example 1-3).

Example 1-4

Halloysite was surface-modified by the same procedure as in Example 1-1 except for using the halloysite (containing halloysite in nanotube form (halloysite nanotubes)) (surface hydroxy group amount: 2.5 mmol/g) available from Sigma-Aldrich described above in place of the purified halloysite 1.

From the FT-IR measurement, it was confirmed that the halloysite after the surface modification was halloysite having carboxy group-containing groups (—COCH$_2$OCH$_2$—COOH) on the inner surfaces of the halloysite nanotubes (surface-modified halloysite). Note that each carboxy group-containing group was bonded to the alumina on the inner surface of the halloysite nanotube and formed a structure represented by Al—O—COCH$_2$OCH$_2$—COOH.

When the thermogravimetry-differential thermal analysis (TG-DTA) was performed on the obtained surface-modified halloysite, the carboxy group content was estimated as 0.3 mmol/g.

Example 1-6

The obtained purified halloysite 1 was dried at 150° C. for 1 hour. Thereafter, pulverization was performed until the form of the nanotubes was totally broken to obtain a pulverized product of the purified halloysite 1 (purified halloysite 1 pulverized product) that did not contain halloysite in nanotube form. Thereafter, the purified halloysite 1 pulverized product was surface-modified by the same procedure as in Example 1-1 except for using the purified halloysite 1 pulverized product in place of the purified halloysite 1.

From the FT-IR measurement, it was confirmed that the halloysite after the surface modification was halloysite having carboxy group-containing groups (—COCH$_2$OCH$_2$—COOH) on the surface of the halloysite (surface-modified halloysite). Note that each carboxy group-containing group was bonded to the alumina on the surface of the halloysite nanotube and formed a structure represented by Al—O—COCH$_2$OCH$_2$—COOH.

When the thermogravimetry-differential thermal analysis (TG-DTA) was performed on the obtained surface-modified halloysite, the carboxy group content was estimated as 0.6 mmol/g.

Example 1-7

The purified halloysite 2 was surface-modified by the same procedure as in Example 1-1 except for using the purified halloysite 2 in place of the purified halloysite 1.

From the FT-IR measurement, it was confirmed that the halloysite after the surface modification was halloysite having carboxy group-containing groups (—COCH$_2$OCH$_2$—COOH) on the inner surfaces of the halloysite nanotubes (surface-modified halloysite). Note that each carboxy group-containing group was bonded to the alumina on the inner surface of the halloysite nanotube and formed a structure represented by Al—O—COCH$_2$OCH$_2$—COOH.

When the thermogravimetry-differential thermal analysis (TG-DTA) was performed on the obtained surface-modified halloysite, the carboxy group content was estimated as 0.6 mmol/g.

Note that the surface-modified halloysites of Examples 1-1 to 1-4 and Examples 1-6 and 1-7 were halloysites further containing hydroxy groups on their surfaces.

Because no interaction between carboxy group-containing groups was observed in the FT-IR spectra of the surface-modified halloysites of Examples 1-1 to 1-3 and Examples 1-6 and 1-7, it was found that the carboxy group-containing groups and the hydroxy groups coexisted uniformly on the surfaces of the surface-modified halloysites of Examples 1-1 to 1-3 and Examples 1-6 and 1-7.

Example 2-1

The obtained purified halloysite 1 was dried at 150° C. for 1 hour. To the dried purified halloysite 1 (0.20 g), 10 mL of anhydrous toluene and 25 mmol of 1,3-propanesultone (35.2 equivalents relative to the surface hydroxy group amount of the halloysite) were added, and the mixture was subjected to ultrasonic treatment for 1 hour and then agitated while being refluxed (120° C., 72 hours). Subsequently, after the filtration, the resultant was washed with distilled water and subjected to drying treatment. Thus, the purified halloysite 1 was surface-modified.

Figure 3:
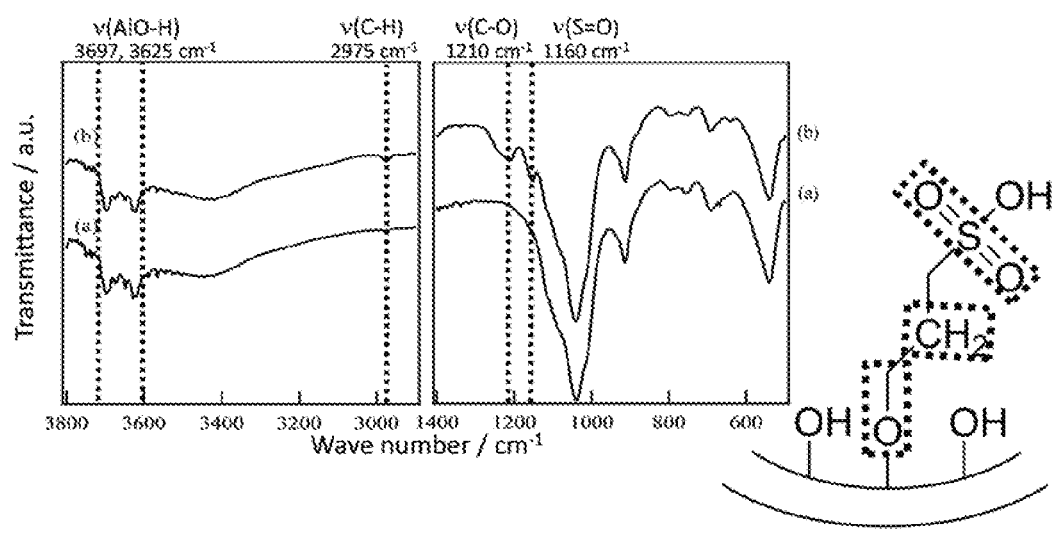
FIG. 3 shows FT-IR spectra of halloysite before and after surface modification.

FIG. 3 is spectra obtained by Fourier Transform Infrared Spectroscopy (FT-IR) of the halloysite before and after surface modification. (a) is the spectrum before the surface modification, and (b) is the spectrum after the surface modification. From the FT-IR measurement, it was confirmed that the obtained halloysite was halloysite having sulfo group-containing groups (—C$_3$H$_6$—SO$_3$H) on the inner surfaces of the halloysite nanotubes (surface-modified halloysite). Note that each sulfo group-containing group was bonded to the alumina on the inner surface of the halloysite nanotube and formed a structure represented by Al—O—C$_3$H$_6$—SO$_3$H.

When the thermogravimetry-differential thermal analysis (TG-DTA) was performed on the obtained surface-modified halloysite, the sulfo group content was estimated as 1.4 mmol/g.

Example 2-2

Halloysite was surface-modified by the same procedure as in Example 2-1 except for using the halloysite (containing halloysite in nanotube form (halloysite nanotubes)) (surface hydroxy group amount: 2.5 mmol/g) available from Sigma-Aldrich described above in place of the purified halloysite 1.

From the FT-IR measurement, it was confirmed that the halloysite after the surface modification was halloysite having sulfo group-containing groups (—C$_3$H$_6$—SO$_3$H) on the inner surfaces of the halloysite nanotubes (surface-modified halloysite). Note that each sulfo group-containing group was bonded to the alumina on the inner surface of the halloysite nanotube and formed a structure represented by Al—O—C$_3$H$_6$—SO$_3$H.

When the thermogravimetry-differential thermal analysis (TG-DTA) was performed on the obtained surface-modified halloysite, the sulfo group content was estimated as 0.7 mmol/g.

Example 2-7

The purified halloysite 1 pulverized product was surface-modified by the same procedure as in Example 2-1 except for using the purified halloysite 1 pulverized product in place of the purified halloysite 1.

From the FT-IR measurement, it was confirmed that the halloysite after the surface modification was halloysite having sulfo group-containing groups (—C$_3$H$_6$—SO$_3$H) on the surface of the halloysite (surface-modified halloysite). Note that each sulfo group-containing group was bonded to the alumina on the surface of the halloysite and formed a structure represented by Al—O—C$_3$H$_6$—SO$_3$H.

When the thermogravimetry-differential thermal analysis (TG-DTA) was performed on the obtained surface-modified halloysite, the sulfo group content was estimated as 1.4 mmol/g.

Example 2-8

The purified halloysite 2 was surface-modified by the same procedure as in Example 2-1 except for using the purified halloysite 2 in place of the purified halloysite 1.

From the FT-IR measurement, it was confirmed that the halloysite after the surface modification was halloysite having sulfo group-containing groups ($—C_3H_6—SO_3H$) on the inner surfaces of the halloysite nanotubes (surface-modified halloysite). Note that each sulfo group-containing group was bonded to the alumina on the surface of the halloysite and formed a structure represented by $Al—O—C_3H_6—SO_3H$.

When the thermogravimetry-differential thermal analysis (TG-DTA) was performed on the obtained surface-modified halloysite, the sulfo group content was estimated as 1.4 mmol/g.

Note that the surface-modified halloysites of Examples 2-1, 2-2, 2-7, and 2-8 were halloysites further containing hydroxy groups on their surfaces.

Furthermore, because no interaction between sulfo group-containing groups was observed in the FT-IR spectra of the surface-modified halloysites of Examples 2-1, 2-7, and 2-8, it was found that the sulfo group-containing groups and the hydroxy groups coexisted uniformly on the surfaces of the surface-modified halloysites of Examples 2-1, 2-7, and 2-8 (those groups were uniformly distributed at a rate of one sulfo group-containing group per 2.54 (=3.55 (mmol/g)/1.4 mmol (mmol/g)) hydroxy groups).

[Catalytic Reaction Using Surface-Modified Halloysite (Hs—COOH)]

In a reaction vessel, 0.02 g of each of the obtained surface-modified halloysites (Examples 1-1 to 1-4, 1-6, and 1-7), 0.1 mmol of cellobiose, and 5 mL of water were added and agitated. Hydrolysis of the cellobiose was performed by using the surface-modified halloysite as a solid catalyst (150° C., 8 hours).

Furthermore, by using the surface-modified halloysite of Example 1-3, hydrolysis of the cellobiose was performed in the same manner except for extending the hydrolysis time to 24 hours (Example 1-5).

Furthermore, hydrolysis of the cellobiose was performed in the same manner except for using the purified halloysite 1 described above (surface-unmodified product) in place of the surface-modified halloysite (Comparative Example 1-1).

The yield (yield of glucose) and selectivity (proportion of glucose relative to reacted cellobiose) are shown in Table 1 below. Note that the yield and the selectivity were determined by using High Performance Liquid Chromatography (HPLC).

TABLE 1

| | Solid catalyst | Carboxy group content [mmol/g] | Substitution rate (mol %) | Reaction time [hour] | Yield (%) | Selectivity (%) |
|---|---|---|---|---|---|---|
| Comparative Example 1-1 | Hs (Purified halloysite 1) | 0.0 | 0% | 8 | 7.8 | 99 |
| Example 1-1 | Hs-COOH (Purified halloysite 1) | 0.6 | 17% | 8 | 11.1 | 91.1 |
| Example 1-2 | Hs-COOH (Purified halloysite 1) | 0.9 | 25% | 8 | 13.2 | 96.1 |
| Example 1-3 | Hs-COOH (Purified halloysite 1) | 2.8 | 79% | 8 | 22.3 | 93.0 |
| Example 1-4 | Hs-COOH (SIGMA-ALDRICH) | 0.3 | 12% | 8 | 8.9 | 86.5 |
| Example 1-5 | Hs-COOH (Purified halloysite 1) | 2.8 | 79% | 24 | 51.4 | 89.3 |
| Example 1-6 | Hs-COOH (Purified halloysite 1 pulverized product) | 0.6 | 17% | 8 | 8.5 | 85.0 |
| Example 1-7 | Hs-COOH (Purified halloysite 2) | 0.6 | 17% | 8 | 12.5 | 95.0 |

Note that, in Table 1, "Hs—COOH" represents the surface-modified halloysite (Hs—COOH), and "Hs" represents halloysite (surface-unmodified halloysite). "Carboxy group content" represents the carboxy group content described above. "Substitution rate" represents the substitution rate described above. Furthermore, "reaction time" represents the time period during which the hydrolysis of the cellobiose was performed.

As shown in Table 1, when the surface-modified halloysites of Examples 1-1 to 1-4, 1-6, and 1-7, which were halloysites having carboxy group-containing groups on their surfaces, were used as the solid catalysts, glucose was obtained in a high yield. That is, the surface-modified halloysites of Examples 1-1 to 1-4, 1-6, and 1-7, which were halloysites having carboxy group-containing groups on their surfaces, exhibited high catalytic activity. In particular, Examples 1-1 to 1-4 and 1-7, in which at least part of the halloysite was in nanotube form, exhibited higher catalytic activity. Among these, Examples 1-1 to 1-3 and 1-7, which were produced by using the purified halloysite corresponded to the powder of the present invention described above, exhibited even higher catalytic activity. It is conceived that, while the halloysite available from Sigma-Aldrich used in Example 1-4 contained a large amount of impurities (quartz and gibbsite), the purified halloysite used in Examples 1-1 to 1-3 and 1-7 had a small amount of impurities (FIG. 2) and thus exhibited even higher catalytic activity.

Furthermore, among Examples 1-1 to 1-3 and 1-7, comparing Example 1-1 and Example 1-7 in which the carboxy group content was 0.6 mmol/g, Example 1-7 which used the purified halloysite obtained through spray drying exhibited even higher catalytic activity.

Furthermore, comparing Examples 1-1 to 1-3 (comparing the embodiments that used the purified halloysites obtained through media slurry drying), Examples 1-2 and 1-3, in which the carboxy group content was not less than 0.7 mmol/g, exhibited even higher catalytic activity. Among these, Example 1-3, in which the carboxy group content was not less than 1.0 mmol/g, exhibited still even higher catalytic activity.

When xylan, which is a polysaccharide, was hydrolyzed by using the surface-modified halloysite of Example 1-3 as a solid catalyst, xylose was obtained in a high yield (89.3%).

Furthermore, comparing Examples 1-3 and 1-5 (comparing the embodiments different only in reaction time was), Example 1-5, in which the reaction time was not shorter than 10 hours, achieved even higher yield.

[Catalytic Reaction Using Surface-Modified Halloysite (Hs-PS)]

In a reaction vessel, 30 mg of each of the obtained surface-modified halloysites (Examples 2-1, 2-2, 2-7, and 2-8), 20 mg of fructose, 16 mg of ethylene glycol, and 5 mL of 2-butanol were added and agitated. Dehydration and decomposition of the fructose was performed by using the surface-modified halloysite as a solid catalyst (120° C., 24 hours).

Furthermore, 20 mg of the surface-modified halloysite of Example 2-1, 40 mg of fructose, and 2 mL of the solvent described in Table 2 below were added in a reaction vessel and agitated. Dehydration and decomposition of the fructose was performed by using the surface-modified halloysite as a solid catalyst (120° C., 2 hours) (Examples 2-3 to 2-5).

Furthermore, dehydration and decomposition of the fructose was performed by the same procedure as in Example 2-1 except for changing the time for dehydration and decomposition to 4 hours (Example 2-6).

Furthermore, dehydration and decomposition of the fructose was performed by the same procedure as in Example 2-3 except for adding no surface-modified halloysite (Comparative Example 2-1).

Furthermore, dehydration and decomposition of the fructose was performed by the same procedure as in Example 2-3 except for using the purified halloysite 1 described above (surface-unmodified product) in place of the surface-modified halloysite (Comparative Example 2-2).

Furthermore, dehydration and decomposition of the fructose was performed by the same procedure as in Example 2-6 except for adding no surface-modified halloysite (Comparative Example 2-3).

Furthermore, dehydration and decomposition of the fructose was performed by the same procedure as in Example 2-6 except for using the purified halloysite 1 described above (surface-unmodified product) in place of the surface-modified halloysite (Comparative Example 2-4).

Reaction conversion rate and yield (yield of hydroxymethylfurfural (HMF) which was the desired substance) are shown in Table 2 below. Note that the reaction conversion rate and the yield were determined by using High Performance Liquid Chromatography (HPLC).

TABLE 2

| | Solid catalyst | Sulfo group content [mmol/g] | Substitution rate (mol %) | Reaction time [hour] | Solvent | Reaction conversion rate (%) | Yield (%) |
|---|---|---|---|---|---|---|---|
| Example 2-1 | Hs-PS (Purified halloysite 1) | 1.4 | 39% | 24 | 2-Butanol | 95.0 | 92.4 |
| Example 2-2 | Hs-PS (SIGMA-ALDRICH) | 0.7 | 28% | 24 | 2-Butanol | 66.5 | 46.2 |
| Example 2-3 | Hs-PS (Purified halloysite 1) | 1.4 | 39% | 2 | 2-Butanol | 67.2 | 31.0 |
| Example 2-4 | Hs-PS (Purified halloysite 1) | 1.4 | 39% | 2 | Ethanol | 33.3 | 11.5 |
| Example 2-5 | Hs-PS (Purified halloysite 1) | 1.4 | 39% | 2 | 2-Propanol | 76.5 | 12.6 |
| Example 2-6 | Hs-PS (Purified halloysite 1) | 1.4 | 39% | 4 | 2-Butanol | 33.0 | 32.0 |
| Example 2-7 | Hs-PS (Purified halloysite 1 pulverized product) | 1.4 | 39% | 24 | 2-Butanol | 50.0 | 30.0 |
| Example 2-8 | Hs-PS (Purified halloysite 2) | 1.4 | 39% | 24 | 2-Butanol | 97.0 | 95.0 |
| Comparative Example 2-1 | None | — | — | 2 | 2-Butanol | 0 | 0 |

TABLE 2-continued

| Solid catalyst | | Sulfo group content [mmol/g] | Substitution rate (mol %) | Reaction time [hour] | Solvent | Reaction conversion rate (%) | Yield (%) |
|---|---|---|---|---|---|---|---|
| Comparative Example 2-2 | Hs (Purified halloysite 1) | 0.0 | 0% | 2 | 2-Butanol | 0 | 0 |
| Comparative Example 2-3 | None | — | — | 4 | 2-Butanol | 0 | 0 |
| Comparative Example 2-4 | Hs (Purified halloysite 1) | 0.0 | 0% | 4 | 2-Butanol | 0 | 0 |

Note that, in Table 2, "Hs-PS" represents the surface-modified halloysite (Hs-PS), and "Hs" represents halloysite (surface-unmodified halloysite). "Sulfo group content" represents the sulfo group content described above. "Substitution rate" represents the substitution rate described above. "Reaction time" represents the time period during which the dehydration and decomposition of fructose were performed.

As shown in Table 2, when the surface-modified halloysites of Examples 2-1 to 2-8, which were halloysites having sulfo group-containing groups on their surfaces, were used as the solid catalysts, HMF was obtained in a high yield. That is, the surface-modified halloysites of Examples 2-1 to 2-8, which were halloysites having sulfo group-containing groups on their surfaces, exhibited high catalytic activity.

Comparing Examples 2-1, 2-2, 2-7, and 2-8 (comparing the embodiments in which the reaction time was 24 hours), Examples 2-1, 2-2, and 2-8, in which at least part of the halloysite was in tube form, exhibited higher catalytic activity. Among these, Examples 2-1 and 2-8, which were produced by using the purified halloysite corresponding to the powder of the present invention described above, exhibited even higher catalytic activity. It is conceived that, while the halloysite available from Sigma-Aldrich used in Example 2-2 contained a large amount of impurities (quartz and gibbsite), the purified halloysite used in Examples 2-1 and 2-8 had a small amount of impurities (FIG. 2) and thus exhibited even higher catalytic activity. Among Examples 2-1 and 2-8, Example 2-8 which used the purified halloysite obtained through spray drying exhibited still even higher catalytic activity.

Comparing Examples 2-3 to 2-5 (comparing the embodiments in which the reaction time was 2 hours), Examples 2-3 and 2-4, which used an alcohol having at least 3 carbon atoms as a reaction solvent, achieved even higher yield. Among these, Example 2-3, which used an alcohol having at least 4 carbon atoms as a reaction solvent, achieved even higher yield.

Furthermore, comparing Examples 2-1, 2-3, and 2-6 (comparing the embodiments different only in reaction time), Examples 2-1 and 2-6, in which the reaction time was not shorter than 3 hours, achieved even higher yield. Among these, Example 2-1, in which the reaction time was not shorter than 10 hours, achieved even higher yield. It is conceived that, by extending the reaction time, a dimer of fructose generated as an intermediate was converted to HMF.

The invention claimed is:

1. A surface-modified halloysite having a carboxy group-containing group —L—COOH, wherein L is a single bond or a divalent organic group, or a sulfo group-containing group —L—SO$_3$H, wherein L is a single bond or a divalent organic group, on its surface, wherein the carboxy group-containing group -L-COOH and the sulfo group-containing group —L—SO$_3$H are directly bonded to the surface, and wherein the divalent organic group is divalent aliphatic hydrocarbon groups, divalent aromatic hydrocarbon groups, —O—, —S—, —SO$_2$—, —NR— (R: hydrocarbon group), —CO—, —NH—, —COO—, —CONH—, or groups formed from combinations of these.

2. The surface-modified halloysite according to claim 1 further having a hydroxy group on its surface.

3. The surface-modified halloysite according to claim 2, wherein at least part of the surface-modified halloysite is in nanotube form.

4. A catalytic reaction using the surface-modified halloysite described in claim 3 as a solid catalyst.

5. A catalytic reaction using the surface-modified halloysite described in claim 3 as a solid catalyst,
wherein, using the surface-modified halloysite as a solid catalyst, a polysaccharide is hydrolyzed to synthesize a monosaccharide or fructose is dehydrated and decomposed to synthesize hydroxymethylfurfural.

6. A surface-modified halloysite producing method comprising reacting halloysite with a carboxylic anhydride or a cyclic sulfonic acid ester to thereby produce the surface-modified halloysite described in claim 2.

7. A catalytic reaction using the surface-modified halloysite described in claim 2 as a solid catalyst.

8. A catalytic reaction using the surface-modified halloysite described in claim 2 as a solid catalyst, wherein a polysaccharide is hydrolyzed to synthesize a monosaccharide or fructose is dehydrated and decomposed to synthesize hydroxymethylfurfural.

9. The surface-modified halloysite according to claim 1, wherein at least part of the surface-modified halloysite is in nanotube form.

10. A surface-modified halloysite producing method comprising reacting halloysite containing halloysite in nanotube form with a carboxylic anhydride or a cyclic sulfonic acid ester to thereby produce the surface-modified halloysite described in claim 9.

11. A catalytic reaction using the surface-modified halloysite described in claim 9 as a solid catalyst.

12. A catalytic reaction using the surface-modified halloysite described in claim 3 as a solid catalyst,
wherein, using the surface-modified halloysite as a solid catalyst, a polysaccharide is hydrolyzed to synthesize a monosaccharide or fructose is dehydrated and decomposed to synthesize hydroxymethylfurfural.

13. A surface-modified halloysite producing method comprising reacting halloysite with a carboxylic anhydride or a cyclic sulfonic acid ester to thereby produce the surface-modified halloysite described in claim 1.

14. A catalytic reaction using the surface-modified halloysite described in claim 1 as a solid catalyst.

15. A catalytic reaction using the surface-modified halloysite of claim 1, wherein, using the surface-modified halloysite as a solid catalyst, a polysaccharide is hydrolyzed to synthesize a monosaccharide or fructose is dehydrated and decomposed to synthesize hydroxymethylfurfural.

16. The surface-modified halloysite according to claim 1, wherein the surface-modified halloysite is a surface-modified halloysite having the carboxy group-containing group on its surface.

17. The surface-modified halloysite according to claim 1, wherein the surface-modified halloysite is a surface-modified halloysite having the sulfo group-containing group on its surface.

18. The surface-modified halloysite according to claim 1, wherein a halloysite before surface modification of the surface-modified halloysite is halloysite powder containing granules formed by causing halloysite containing halloysite nanotubes to aggregate, the granules having first pores derived from tube pores of the halloysite nanotubes and second pores that are different from the first pores.

\* \* \* \* \*